United States Patent [19]
Gately

[11] Patent Number: 5,866,706
[45] Date of Patent: Feb. 2, 1999

[54] PREPARATION AND SEPARATION OF RAC AND MESO COMPOUND MIXTURES

[75] Inventor: Daniel Anthony Gately, Keenesburg, Colo.

[73] Assignee: Boulder Scientific Co., Mead, Colo.

[21] Appl. No.: 871,662

[22] Filed: Jun. 9, 1997

[51] Int. Cl.$^6$ .................................................... C07F 7/08
[52] U.S. Cl. ........................... 556/431; 556/11; 585/22; 585/27; 585/360; 585/478
[58] Field of Search .................. 556/431, 11; 585/22, 585/27, 360, 478

[56] References Cited

U.S. PATENT DOCUMENTS

| | | | |
|---|---|---|---|
| 5,585,509 | 12/1996 | Langhauser et al. | 556/11 |
| 5,670,683 | 9/1997 | Langhauser et al. | 556/11 X |
| 5,719,251 | 2/1998 | Wilczek et al. | 556/431 X |

*Primary Examiner*—Paul F. Shaver
*Attorney, Agent, or Firm*—Edward S. Irons

[57] ABSTRACT

Utilization of thermodynamic ratios to produce pure rac and pure meso isomers or a mixture thereof.

31 Claims, No Drawings

PREPARATION AND SEPARATION OF RAC AND MESO COMPOUND MIXTURES

FIELD OF INVENTION

This invention relates to the preparation and separation of mixtures of rac and meso forms of symmetrical compounds. More particularly, the invention relates to the preparation and separation of rac and meso metallocene catalyst ligand mixtures.

BACKGROUND OF THE INVENTION

Protocols for the preparation of isospecific α-olefin polymers may require use of only the substantially pure rac isomer of a symmetrical metallocene catalyst. Likewise, only the meso isomer is useful to implement certain non-isospecific α-olefin polymerization protocols. Typical metallocene catalyst ligand synthesis yields a mixture containing about equal amounts of the meso and rac isomers. Consequently, half of the chemicals used in the ligand synthesis is wasted. Various metallocene α-olefin isospecific polymerization catalysts which have no meso form have been suggested to solve this problem. See, e.g., European patent EP 544,308 and U.S. Pat. No. 5,612,428.

A need exists for technology practically useful to resolve mixtures of rac and meso metallocene ligands, and to convert substantially pure rac and meso metallocene ligands to the correspondingly substantially pure meso or the correspondingly substantially pure rac isomers.

DEFINITIONS AND SYMBOLS

Hydrocarbyl group—a saturated or unsaturated aliphatic or aromatic, substituted or unsubstituted hydrocarbyl group. Alkyl groups of 1 to 6 carbon atoms are preferred.

bisEBI—bis indenyl ethane.

TAS—Trialkyl silyl in which A is a one to six carbon atom hydrocarbyl group.

TMS—trimethyl silyl $Si(CH_3)_3$.

(TMS)EBI—bis(trimethyl silyl) bis indenyl ethane.

(TMS)(EB2MeI)—bis(trimethyl silyl) bis 2 methyl indenyl ethane.

(TMS)(EB4,7MeI)—bis(trimethyl silyl) bis 4,7 dimethyl indene.

$Cp_1$—Q—$Cp_2$—a symmetrical compound, e.g., a metallocene catalyst ligand in which $Cp_1$ and $CP_2$ are identical cyclopentadienyl groups, wherein Q is a bridge connecting $Cp_1$ and $CP_2$ and wherein $Cp_1$ and $Cp_2$ have a TAS substituent or a one to six carbon atom hydrocarbyl substituent in at least the 2 or 4 positions with respect to the bridge Q and wherein the bridge Q is an alkylene group $—(CH_2)_n—$ in which n is a one to six carbon atom hydrocarbyl group, preferably a methyl group or optionally a silandiyl group having the formula

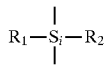

in which $R_1$ and $R_2$ are the same or optionally different one to six carbon atom hydrocarbyl groups. $R_1$ and $R_2$ are each preferably a methyl group.

Substantially pure—at least 96% pure by gas chromatograph mass spectrometry (GCMS).

Thermodynamic conditions—temperature, time, pressure, the presence or absence of air or inert atmosphere, and the presence or absence of a non—interfering liquid medium.

Thermodynamic ratio—the ratio of the molecular proportions of the rac and meso forms of a symmetrical compound which ratio is produced by a specific thermodynamic condition or set of thermodynamic conditions. A thermodynamic ratio may be produced in either the presence or absence of a liquid medium in which the symmetrical compound is contained when the thermodynamic condition or et of thermodynamic conditions is determined.

SUMMARY OF THE INVENTION

It has been discovered that the relative molecular proportions (thermodynamic ratio) of rac and meso forms of a symmetrical compound of formula $Cp_1$—Q—$Cp_2$— is a function of the thermodynamic conditions to which the compound is or has been subjected. The discovery of the thermodynamic ratios of such compounds in combination with the known or readily determinable differential solubility thereof affords a practical method for producing pure rac or pure meso isomers form a mixture thereof such as that which may be produced by conventional metallocene ligand synthesis protocols and for the conversion of either isomer to a substantially pure form of the other isomer.

In this context, thermodynamic conditions include temperature, time, pressure, the presence of absence of air or inert atmosphere and the presence or absence of non-interfering liquid media. For example, 100% rac-bis(TMS) EBI heated at atmospheric pressure in air to a temperature of 150° C. to 200° C. for a time period of 0.5 to 2.5 hours results in a mixture in which the rac/meso forms are present in a thermodynamic ratio of about 60% to 40%. Like treatment of pure meso isomers results in a similar thermodynamic ratio of the meso and rac forms.

The invention may comprise iterated heating steps in which a first mixture of rac and meso forms is converted to a second mixture enriched either in the rac form or in the meso form and in which the rac and meso forms are present in the thermodynamic ratio unique to the thermodynamic (heat) condition imposed. The rac and meso components are separated from the second mixture by solvent fractionation and either of the separated rac or meso forms converted to a third, thermodynamic ratio mixture. The separation and thermodynamic treatment steps are repeated until the thermodynamic ratio of one of the rac or meso isomers is at least 9:1 and preferably until a substantially pure, e.g., 96% pure rac or meso product results. The iterated heating steps are preferably conducted in the absence of water to avoid the formation of undesirable silanols which may adversely affect metallocene catalysts.

The invention may also include production of a metallocene α-olefin polymerization catalyst by reaction of the substantially pure rac or meso ligand or a mixture thereof in a thermodynamic ratio with zirconium tetrachloride. The synthesis protocol entails preparing a solution of the ligand in methylene chloride, adding zirconium tetrachloride to the solution wherein the metallocene catalyst forming reaction occurs, removing the methylene chloride solvent, dispersing and washing the residual solid in ethyl ether, washing the residual solid with methanol, removing the methanol, washing the residual solid with ethyl ether and ultimately filtering and drying the metallocene catalyst so produced.

DETAILED DESCRIPTION OF THE INVENTION

This invention is useful to resolve mixtures of meso and rac forms of compounds. It has particular applicability to the resolution of symmetrical metallocene catalyst ligands.

In the preferred practice of the invention, compounds of the formula $Cp_1$—Q—$Cp_2$ are isolated in a substantially pure rac or meso isomer. In one embodiment, the invention is applied to resolve mixtures of meso and rac (TMS)EBI; TMS(EB2MeI); and (TMS)EB4,7MeI). Alternatively, the invention is used to prepare substantially pure rac ligands from pure meso ligands and conversely.

Pursuant to one embodiment of the invention, a meso isomer of a metallocene ligand having the formula $Cp_1$—$Cp_2$ is heated at atmospheric pressure in air and in the absence of any liquid medium including water, to a temperature of 150° C.–200° C., preferably 160° C. to 200° C. for a time period requisite to isomerize at least about 10% of said meso isomer to rac isomer wherein a thermodynamic ratio mixture containing 90% meso and 10% rac isomer is produced. Preferably the heating is continued until at least 50% of the meso isomer is converted to rac and wherein a thermodynamic mixture of at least equal molecular amounts of meso and rac isomer is produced. Alternatively, this conversion step of the invention may be accomplished in a non-aqueous, non-interfering liquid medium; for example, tetrahydrofuran (THF). The conversion may also be completed in an aqueous medium but with concurrent production of undesirable silanols.

The meso component of the mixture is separated by solvent fractionation using a solvent, e.g., a 6 to 8 carbon atom alkane, in which only the meso isomer is soluble. The meso isomer solution is cooled, e.g., to about −20° C., the meso isomer precipitate which is subjected to an iteration of heat treatment and solvent fractionation steps as described to provide as a final product of a thermodynamic mixture desired rac content.

Typically the iteration is continued until substantially pure rac product is obtained.

Alternatively, the rac isomer may be converted to the meso isomer in a similar series of iterated steps.

The invention includes reaction of the substantial rac isomer with a Group IV metal halide wherein a metallocene olefin polymerization catalyst is produced as illustrated by Example 4.

EXEMPLIFICATION OF THE INVENTION

EXAMPLE 1

(Aqueous System) (Product May Contain Silanols)
A. Preparation of Mixture of Rac/Meso-bis(TMS)EBI A 12 L flask was charged with bis(indenyl)ethane (EBI) (2 mol, 517 g) and THF (5 L). The solution was cooled (−20° C.) and then treated with BuLi (4.24 mol, 2.65 L). After two hours at room temperature (RT), the Li$_2$EBI was transferred by cannula to a separate 12 L flask containing neat TMSCl (6.07 mol, 660g, 770 mL). After 12 hours, the solution was treated with water (3 L) at RT that resulted in a 20° C. exotherm. The organic layer was separated from the aqueous phase, the aqueous phase was extracted with Et$_2$O (2×1 L), and the combined extracts were distilled affording a residue that contained rac-/meso-bis(TMS)EBI in a 50/50 ratio. Yield: 788 g, 97.8%, 98% pure by GCMS (gas chromatograph mass spectrography). See Equation 1.

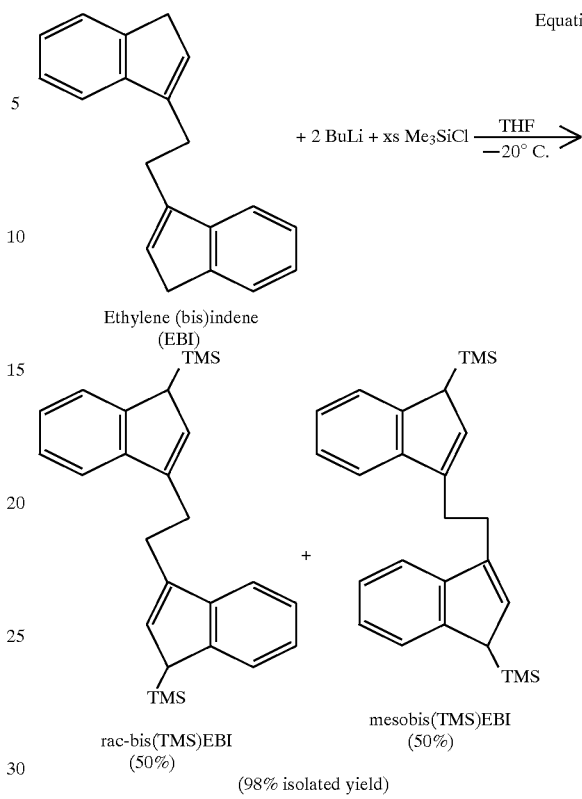

Equation 1

The mixture of rac-/meso-bis(TMS)EBI was treated with hexanes (2.37 L, 2.4 mL/g), the solution was cooled (−20° C.) and then filtered in a tarred 12 L flask. The solid meso-bis(TMS)EBI was put into a tarred 5 L flask and dried. Yield: 340 g, 43% from pure meso-bis(TMS)EBI.
B. Conversion of the Meso-bis(TMS) EBI of Example 1A to Rac-bis(TMS) EBI The following procedures (A–C) were repeated until a small amount of the pure meso-bis(TMS)EBI remained (Equations 2 and 3 below).

(A) The meso-bis(TMS)EBI (340 g) was heated (200° C.) neat for one hour. (B) The residue was cooled to ~50° C., and then treated with hexanes (1.02 L, 2.4 mL/g). (C) The solution was stirred and then cooled (−20° C.), and the solution was filtered into the same tarred 12 L flask that was used above.

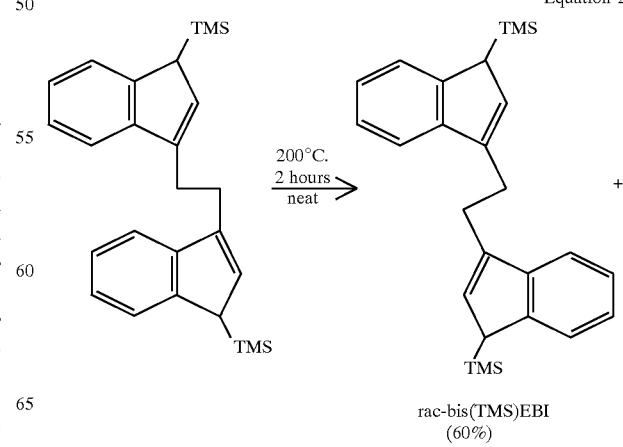

Equation 2

-continued

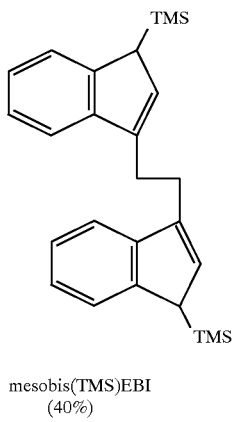

mesobis(TMS)EBI
(40%)

The recovered solid meso-bis(TMS)EBI was dried and three iterations (steps A–C) were performed (Equation 3); after the fourth run, the remaining meso-bis(TMS)EBI was saved.

Equation 3

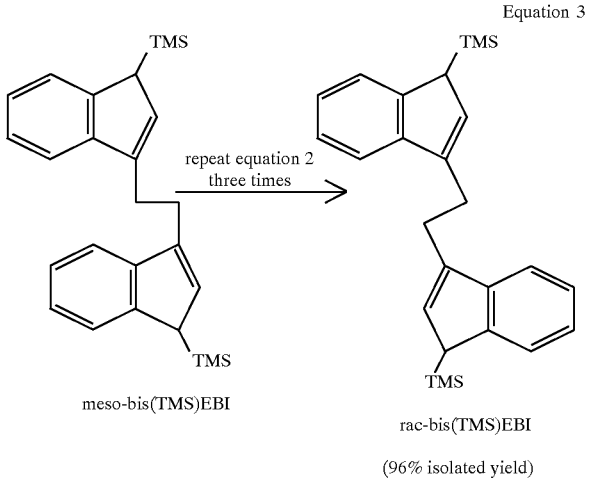

meso-bis(TMS)EBI → rac-bis(TMS)EBI (96% isolated yield)

The hexanes from the filtrate collected after all four iterations in the tarred 12 L flask was distilled (careful to avoid a temperature rise >120° C. of the residue) and the residue was dried overnight under a high vacuum (at least 1 mm Hg) affording a viscous oil that slowly solidified to a soft golden- or brown-colored paste. Yield of rac-bis(TMS)EBI: 754 g (93.6% from EBI in Equation 1; 95.7% from meso-bis(TMS)EBI in Equations 2 and 3; 98% pure by GCMS.

EXAMPLE 2

Preparation of Rac-(ethylene-bis Indenyl) Zirconium Dichloride

The tarred 12 L flask containing rac-bis(TMS)EBI (1.87 mol, 754 g) from Example 1 was treated with $CH_2Cl_2$ (800 mL, pre-treated with molecular sieves) and the solution was transferred to a 5 L flask. To this solution was added $ZrCl_4$ (1.87 mol, 437 g) at RT and the solution was stirred for 24 hours. Most of the solvent was removed by distillation (1 atm), then by high vacuum ensuring that most of the TMSCl was removed from the brown solid that contained rac-EBIZrCl$_2$. To the brown solid was added MeOH (2 L) and the resulting yellow slurry was stirred for fifteen minutes and then filtered. The solid was put back into the same 5 L flask and treated with $Et_2O$ (2 L), the solution was stirred for ten minutes, the yellow solid was filtered, washed with $Et_2O$ (500 mL) and dried. Yield of rac-(EBI)ZrCl$_2$; 377 g, 48.0% from rac-bis(TMS)EBI in Equation 3, 44.9% overall yield from EBI in Equation 1, 100% diastereomeric excess by $^1$HNMR.

Equation 4

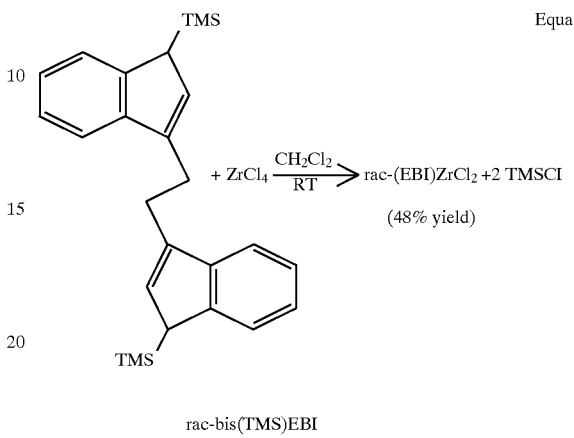

rac-bis(TMS)EBI + $ZrCl_4$ $\xrightarrow{CH_2Cl_2}{RT}$ rac-(EBI)ZrCl$_2$ + 2 TMSCl (48% yield)

EXAMPLE 3

(Non-Aqueous System) (Silanol-Free Product)
A. Preparation of Mixture of Rac/Meso-bis(TMS)EBI (Equation 1)

A 22 L flask was charged with bis(indenyl)ethane (EBI) (1036 g, 4 mol) and THF (10 L). The solution was cooled (–20° C.) and then treated with BuLi (8.484 mol., 5.30 L). After 12 hours at room temperature (RT), the Li$_2$EBI was transferred by cannula to a separate 22 L flask containing neat TMSCl (12.14 mol, 1320 g, 1.54 L). After an additional 12 hours, the solvent was distilled to ~¼ volume before adding heptane (4 L). The solvent was distilled to a slurry (ensuring that all of the THF was removed) and the near solid residue was treated with heptane (3.7 L, assumed 95% yield, 1530 g×2.4 mL/g). The solution was filtered through Celite removing lithium chloride. The filtrate was cooled to –20° C., and the slurry was filtered into a tarred 12 L flask. The filtrate that contained enriched rac-bis(TMS)EBI was saved. The solid meso-bis(TMS)EBI was put into a tarred 5 L flask and dried. Yield of enriched meso-bis(TMS)EBI: 1029 g.

B. Conversion of the Meso-bis(TMS)EBI Product of Example 2A to Rac-bis(TMS)EBI

The following procedures (A–C) were repeated until a small amount of meso-bis(TMS)EBI remained.

The meso-bis(TMS)EBI (1029 g) from Example 2A was heated (200° C.) neat for 1–2 hours. (B) The residue was cooled to ~80° C. and then treated with heptane (2.5 L, 2.4 mL/g). (C) The solution was stirred and then cooled (–20° C.), and the solution was filtered into the same filtrate that was saved above. The recovered solid meso-bis(TMS)EBI was dried and steps A–C were repeated three more times (equation 3); after the last run, the remaining meso-bis(TMS)EBI was saved (126 g, 8%).

The heptane from the filtrate collected in the tarred 12 L flask was distilled (careful to avoid a temperature rise >120° C. of the residue), and the residue was dried under a vacuum (at least 1 mm Hg) so that most of the heptane was removed. The yield of enriched rac-bis(TMS)EBI was 1484 g, 3.66 mol (92%) Yield of rac-bis(TMS)EBI corrected for the amount of meso-bis(TMS)EBI (10%) present in residue: 80% by $^1$H NMR, 1327 g, 82% from EBI in Equation 1.

EXAMPLE 4

Preparation of Rac-EBI)ZrCl$_2$

A tarred 12 L flask containing the about 90:10 rac:meso-bis(TMS)EBI (1484 g, 3.66 mol) Example 3 product was treated with CH$_2$Cl$_2$ (4 L, pre-treated with molecular sieves). To this solution was added ZrCl$_4$ (855 g, 3.67 mol) at RT, and the solution was stirred for 24 hours (during this time, color changed form brown→deep purple→light brown-yellow). The solvent was carefully distilled until the volume was reduced by ~¼. To the brown-yellow slurry was added Et$_2$O (6 L), and the slurry was stirred for 1 hour. The slurry was filtered, the solid was washed with Et$_2$O (2 L), and the solid was put back into the same 12 L flask. The solid was treated with MeOH (6 L), the slurry was stirred for 30 minutes, the slurry was filtered, and the solid was washed with MeOH (2 L). The solid was put back into the same 12 L flask and treated with Et$_2$O (6 L), the slurry was stirred for 30 minutes, and the mustard-yellow solid was filtered and dried. A small sample (~50 mg) was placed in a test-tube and dissolved in CH$_2$Cl$_2$; no appreciable undissolved solids were visible. Yield of rac-(EBI)ZrCl$_2$: 627 g, 47% yield from pure rac-bis(TMS)EBI in equation 3, 37% overall yield from EBI in equation 1, 100% diastereomeric excess ($^1$H NMR). This same procedure has been repeated several times and yields of rac-(EBI)ZrCl$_2$ from pure rac-bis(TMS)EBI are typically 45–55%.

EXAMPLE 5

Pilot Plant Experiment

Examples 3 and 4 were repeated in a pilot plant with an improved overall yield of rac-(EBI)ZrCl$_2$. The following summary reports the quantities of materials used and the yields of products in each step:

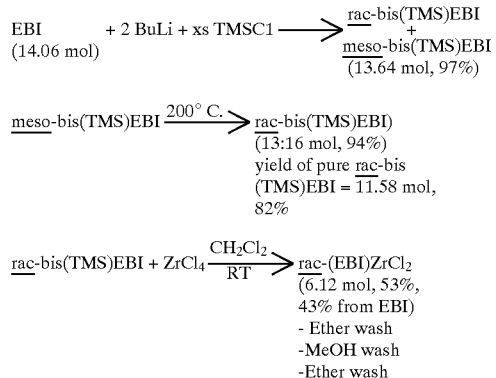

EXAMPLE 6

Example 3 is repeated with the exception that a mixture of rac and meso (TMS)(EB2MeI) is used. The rac TMS ethylene-bis 2-methyl indene produced is reacted with ZrCl$_4$ to produce rac-ethylene-bis(2 methylindenyl) zirconium dichloride.

EXAMPLE 7

Examples 3 is repeated with the exception that a mixture of rac and meso (TMS)(EB4,7MeI) is used, wherein the mixture is enriched in the rac isomer.

The rac TMS(ethylene bis (4,7 dimethyl) indene is reacted with zrcl$_4$ to produce rac 1,2-ethylene bis(4,7 dimethyl indenyl) zirconium dichloride.

I claim:
1. The method which comprises
   (i) providing a first mixture of rac and meso forms at a symmetrical compound
   (ii) subjecting said first mixture of said compound to thermodynamic conditions to provide a second mixture of said rac and meso forms of said compound
   wherein said rac and meso forms of said compound are present in a first thermodynamic ratio in said second mixture
   separating said rac form of said compound or said meso form of said compound from said second mixture;
   subjecting said rac form of said compound or said meso form of said compound as separated from said second mixture to thermodynamic conditions which provide a third mixture of said rac and meso forms of said compound
   wherein said rac and meso forms of said compound are present in said third mixture in a second thermodynamic ratio which may be the same as or different from said first thermodynamic ratio;
   separating said rac form of said compound from said meso form of said compound present in said third mixture.
2. A method which comprises:
   (a) providing a compound which exists in a rac form and in a meso form;
   (b) subjecting said compound to a sequence of thermodynamic conditioning and rac and meso isomer separation steps wherein:
      (i) said thermodynamic conditioning steps are followed by a separation step, and
      (ii) said thermodynamic conditioning steps each comprise subjecting said compound to thermodynamic conditions to provide a thermodynamic mixture of said rac and meso forms of said compound, and wherein
      (iii) each of said separation steps comprises separating said thermodynamic mixture resulting from a preceding thermodynamic treatment step into a rac component and a meso component;
   (c) subjecting either said rac component separated in step (iii) or said meso component separated in step (iii) to at least one iteration of steps (a) and (b).
3. The claim 2 method in which said step (c) iteration of steps (a) and (b) is continued to provide a substantially pure separated rac form or a separated meso form of said compound.
4. The process of claim 1 or claim 2 in which said thermodynamic conditions comprise a temperature of 150° C. to 200° C.
5. The method of claim 1 or claim 2 wherein said compound is a symmetrical metallocene catalyst ligand.
6. The method of claim 1 or claim 2 wherein said compound is bis(trimethyl silyl) bis indenyl ethane or bis (trimethyl silyl) bis-2-methyl indenyl ethane or bis trimethyl silyl bis 4,7 dimethyl indene.
7. The method of claim 1 or claim 2 conducted in the absence of water.
8. The method of claim 1 or claim 2 wherein said thermodynamic treatment step comprises heating said compound to a temperature of 150° C. to 200° C. in the presence of air and in the absence of a liquid medium.
9. The method of claim 2 wherein each of said thermodynamic conditioning steps comprise providing a dispersion of said compound in a non-aqueous, non-interfering liquid medium and subjecting said dispersion to a temperature of 150° C. to 200° C.

10. The method of claim 8 wherein said liquid medium is an aliphatic hydrocarbon.

11. The method of any of claim 1 or claim 9 wherein said compound has the formula $Cp_1$—Q—$Cp_2$, wherein Q is a bridge connecting $Cp_1$ and $Cp_2$ wherein $Cp_1$ and $Cp_2$ have substituents in at least the 2 and 4 positions with respect to the bridge Q and wherein the bridge Q is an alkylene group having one to six carbon atoms or optionally a silandiyl group having the formula

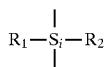

in which $R_1$ and $R_2$ are one to six carbon atom alkyl groups.

12. A method which comprises
(i) providing a first mixture of rac and meso forms of a symmetrical compound having the formula $Cp_1$—Q—$Cp_2$ in which $Cp_1$ and $CP_2$ are identical cyclopentadienyl groups and wherein Q is a bridge connecting $Cp_1$ and $Cp_2$ wherein $Cp_1$ and $Cp_2$ have substituents in at least the 2 and 4 positions with respect to the bridge Q and wherein the bridge Q is an alkylene group having one to six carbon atoms or optionally a silandiyl group having the formula

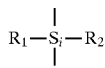

in which $R_1$ and $R_2$ are one to six carbon atom alkyl groups; and
(ii) subjecting said mixture of step (i) to a temperature of 150° C. to 200° C. wherein a second mixture of said rac and meso forms of said symmetrical compound is produced and wherein said second mixture contains a larger proportion than said first mixture of the rac form of said symmetrical compound.

13. The claim 12 method in which said subjecting step (ii) is accomplished in a non-aqueous liquid medium.

14. The claim 12 method further comprising:
(iii) separating said meso and rac components from said second mixture produced in step (ii).

15. The claim 12 method further comprising iterating step (ii) and step (iii) until the rac isomer separated in step (iii) is substantially pure.

16. The claim 12 method further comprising:
(iv) separating said meso and rac components from said second mixture produced in step (ii) and
(v) subjecting the meso component separated in step (iii) to a temperature of 150° C. to 200° C.,
wherein a third mixture of the rac and meso forms of said symmetrical compound is produced, and
(vi) separating said third mixture of rac and meso forms of said symmetrical compounds produced in step (iii) wherein said separated rac form of said symmetrical compound separated in step (vi) is substantially pure.

17. The claim 12 method wherein said $Cp_1$ and $Cp_2$ cyclopentadienyl groups are each substituted at the 2 position with respect to the bridge Q.

18. The claim 12 method wherein said $Cp_1$ and $Cp_2$ cyclopentadienyl groups are substituted by a trimethyl silyl group at the 2 position with respect to the bridge and in which the bridge is —$CH_2CH_2$—.

19. The claim 12 method in which the symmetrical compound is
bis(trimethylsilyl)ethylene bridged indene, or
bis(1 methyl 2 trimethylsilyl ethylene bridged indene, or
bis(2 trimethylsilyl 4,7 dimethyl) ethylene bridged indene.

20. A method which comprises:
(i) reacting bis(indenyl ethane) with n-butyl lithium and trimethyl silyl chloride wherein a first mixture of rac and meso bis(2 trimethylsilyl) ethylene bridged indene is produced;
(ii) heating said first mixture to a temperature of 150° C. to 200° C., wherein a second mixture enriched in rac bis(2-trimethylsilyl)ethylene bridged indene is produced;
(iii) separating said meso component of said first mixture from the rac component of said first mixture;
(iv) heating said separated meso component of said first mixture to a temperature of 150° C. to 200° C. wherein a second mixture having a rac and a component meso is produced;
(v) separating said meso component of said second mixture from said rac component of said second mixture.

21. The claim 20 method in which step (i) is accomplished
(a) in the absence of a liquid medium or
(b) in a non-aqueous liquid medium.

22. A method for converting meso-bis(trimethylsilyl) bis(indenyl)ethane to rac-bis(trimethylsilyl)-bis(indenyl)ethane metallocene catalyst ligand wherein said method comprises iterated steps, and wherein each of said iterated steps comprises heating meso-bis(trimethylsilyl) bis(indenyl)ethane or a mixture thereof with rac-bis(trimethylsilyl) bis(indenyl)ethane to a temperature of at least 100° C. for a time period and under conditions such that a portion of said meso-bis(trimethylsilyl) bis(indenyl)ethane is converted to rac-bis(trimethylsilyl) bis(indenyl)ethane.

23. The claim 22 method wherein said meso-bis(trimethylsilyl) bis(indenyl)ethane is heated to a temperature of 150° C. to 200° C.

24. The claim 22 or claim 23 method wherein said heating is continued for a time period of at least sixty minutes.

25. The claim 22 or 23 method wherein said iterated steps are iterated in a non-aqueous system.

26. A method which comprises:
(i) reacting bis(indenyl)ethane with trimethylsilyl chloride wherein a first reaction mixture of meso-bis(trimethylsilyl) bis(indenyl)ethane and rac-bis(trimethylsilyl) bis(indenyl)ethane is produced; and
(ii) subjecting said first reaction mixture to the method of claim 22 wherein said iterated steps of claim 22 are continued until the claim 22 step (ii) yields a second reaction mixture of meso-bis(trimethylsilyl) bis(indenyl)ethane and rac-bis(trimethylsilyl) bis(indenyl)ethane which contains at least 60% by weight rac-bis(trimethylsilyl) bis(indenyl)ethane.

27. The method for isomerizing meso-bis(trimethylsilyl) bis(indenyl)ethane to rac-bis(trimethylsilyl) bis(indenyl)ethane which comprises heating said meso-bis(trimethylsilyl) bis(indenyl)ethane to a temperature of from 150° C. to 200° C. for a time period of from one hour to three hours, wherein said meso-bis(trimethylsilyl) bis(indenyl)ethane is converted to a mixture containing rac-bis (trimethylsilyl) bis(indenyl)ethane, and meso-bis(trimethylsilyl) bis(indenyl)ethane.

28. The method which comprises:
   (i) providing a meso-bis(trimethylsilyl) bis(indenyl) ethane sample;
   (ii) heating said meso-bis(trimethylsilyl) bis(indenyl) ethane sample of step (i) to a temperature in excess of 100° C. to produce a first product mixture of rac-bis(trimethylsilyl) bis(indenyl)ethane and meso-bis(trimethylsilyl) bis(indenyl)ethane;
   (iii) separating said meso-bis(trimethylsilyl) bis(indenyl) ethane from said first product mixture of step (ii); and
   (iv) heating said meso-bis(trimethylsilyl) bis(indenyl) ethane separated from said first product mixture to a temperature in excess of 100° C. to produce a second product mixture of rac-bis(trimethylsilyl) bis(indenyl)-ethane and meso-bis(trimethylsilyl) bis(indenyl) ethane wherein said second mixture is enriched in the rac-bis(trimethylsilyl) bis(indenyl)-ethane and meso-bis(trimethylsilyl) bis(indenyl)ethane form is produced.

29. A method for producing a metallocene α-olefin polymerization catalyst which comprises:
   (i) providing a catalyst ligand having the formula $Cp_1$—Q—$Cp_2$ wherein Q is a bridge connecting $Cp_1$ and $Cp_2$ wherein $Cp_1$ and $Cp_2$ have substituents in at least the 2 and 4 positions with respect to the bridge Q and wherein the bridge Q is an alkylene group having one to six carbon atoms or optionally a silandiyl group having the formula

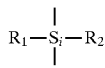

in which $R_1$ and $R_2$ are one to six carbon atom alkyl groups;
   (ii) reacting said catalyst ligand with $ZrCl_4$ in a chlorinated hydrocarbon solvent wherein a reaction mixture containing said metallocene α-olefin polymerization catalyst is synthesized; and
   (iii) separating said catalyst from said reaction mixture.

30. A method for producing a metallocene α olefin polymerization catalyst which comprises:
   (i) dissolving the catalyst ligand produced by the method of claim 22 in methylene chloride;
   (ii) reacting said catalyst ligand with zirconium tetrachloride in said methylene chloride solution;
   (iii) removing the methylene chloride solvent from said solution to provide a solid residue;
   (iv) dispersing said solid residue in methanol;
   (v) separating said residue from said methanol; and
   (vi) washing said separated solid residue with ethyl ester wherein said metallocene α-olefin catalyst is produced.

31. A method for producing a metallocene α olefin polymerization catalyst which comprises:
   (i) dissolving the catalyst ligand produced by the method of claim 22 in methylene chloride;
   (ii) reacting said catalyst ligand with zirconium tetrachloride in said methylene chloride solution;
   (iii) removing the methylene chloride solvent from said solution to provide a solid residue;
   (iv) washing said solid residue separated in step (iii) with ethyl ether;
   (v) dispersing said solid residue separated in step (iv) in methanol;
   (vi) separating said solid residue from said dispersion of step (v); and
   (vii) washing said solid residue separated in step (vi) with ethyl ether.

* * * * *

UNITED STATES PATENT AND TRADEMARK OFFICE
CERTIFICATE OF CORRECTION

PATENT NO. : 5,866,706
DATED : February 2, 1999
INVENTOR(S) : Daniel Anthony Gately It is certified that error appears in the above-identified patent and that said Letters Patent is hereby corrected as shown below:

Column 9,
Line 3, change "8" to -- 9 --.

Column 10,
Line 56, delete "the claim 22 step (ii) yields".
Line 60, before the "." insert -- is produced --.

Signed and Sealed this

Twenty-fifth Day of October, 2005

JON W. DUDAS
*Director of the United States Patent and Trademark Office*